United States Patent
Gauchet

(10) Patent No.: US 6,582,468 B1
(45) Date of Patent: Jun. 24, 2003

(54) INTERVERTEBRAL DISC PROSTHESIS WITH COMPRESSIBLE BODY

(75) Inventor: Fabien Gauchet, Duvy (FR)

(73) Assignee: Spryker Spine (FR)

( * ) Notice: Subject to any disclaimer, the term of this patent is extended or adjusted under 35 U.S.C. 154(b) by 0 days.

(21) Appl. No.: 09/857,655

(22) PCT Filed: Dec. 9, 1999

(86) PCT No.: PCT/FR99/03071

§ 371 (c)(1),
(2), (4) Date: Jun. 7, 2001

(87) PCT Pub. No.: WO00/35383

PCT Pub. Date: Jun. 22, 2000

(30) Foreign Application Priority Data

Dec. 11, 1998 (FR) .............................................. 98 15670

(51) Int. Cl.⁷ ................................................. A61F 2/44
(52) U.S. Cl. ..................... 623/17.16; 623/17; 623/11; 623/12; 623/18; 606/61; 606/86; 606/87; 606/72; 606/73
(58) Field of Search ............................... 623/17, 17.16, 623/11, 12, 18; 606/61, 86, 87, 72, 73

(56) References Cited

U.S. PATENT DOCUMENTS

| | | | | |
|---|---|---|---|---|
| 3,867,728 A | * | 2/1975 | Stubstad et al. ..... | 128/DIG. 21 |
| 4,863,477 A | * | 9/1989 | Monson ................... | 623/17.12 |
| 4,932,969 A | * | 6/1990 | Frey et al. ............... | 623/17.12 |
| 5,002,576 A | * | 3/1991 | Fuhrmann et al. ............ | 606/61 |
| 5,071,437 A | * | 12/1991 | Steffee, Arthur D. ......... | 606/61 |
| 5,123,926 A | * | 6/1992 | Pisharodi ..................... | 606/60 |
| 5,397,364 A | * | 3/1995 | Kozak et al. .................. | 606/61 |
| 5,401,269 A | * | 3/1995 | Buttner-Janz et al. ........ | 606/61 |
| 5,425,773 A | * | 6/1995 | Boyd et al. .............. | 623/17.15 |
| 5,507,816 A | * | 4/1996 | Bullivant ...................... | 606/61 |
| 5,556,431 A | * | 9/1996 | Buttner-Janz ................. | 606/61 |
| 5,674,294 A | * | 10/1997 | Bainville et al. ........ | 623/17.16 |
| 5,676,701 A | * | 10/1997 | Yuan et al. .................... | 606/61 |
| 5,683,465 A | * | 11/1997 | Shinn et al. ............. | 623/17.14 |
| 5,782,832 A | * | 7/1998 | Larsen et al. ................. | 606/61 |
| 5,824,094 A | * | 10/1998 | Serhan et al. ............ | 623/17.16 |
| 5,865,846 A | * | 2/1999 | Bryan et al. ................. | 128/898 |
| 6,052,992 A | * | 4/2000 | Eroshenko .................... | 60/509 |
| 6,179,838 B1 | * | 1/2001 | Fiz ................................ | 606/61 |
| 6,228,118 B1 | * | 5/2001 | Gordon .................... | 623/17.11 |
| 6,348,071 B1 | * | 2/2002 | Steffee et al. ............ | 623/17.15 |
| 6,447,547 B1 | * | 9/2002 | Michelson ............... | 623/17.11 |

FOREIGN PATENT DOCUMENTS

| | | | |
|---|---|---|---|
| DE | 22 63 842 | 12/1972 | |
| DE | 90 00 094 | 1/1990 | |
| EP | 0 277 282 | 10/1987 | |
| EP | 0 356 112 | 12/1993 | |
| FR | 2 723 841 | 8/1994 | |
| GB | 0356112 A1 | * 2/1990 | .................. 623/17 |

* cited by examiner

Primary Examiner—Gregory L. Huson
Assistant Examiner—Azy Kokabi
(74) Attorney, Agent, or Firm—Lerner, David, Littenberg, Krumholz & Mentlik, LLP

(57) ABSTRACT

An intervertebral disc prosthesis comprising two opposing plates and a flexible seal extending between the two opposing plates for forming a closed chamber between the two plates, the flexible seal being adapted to enable the plates to move relative to one another. The disc prosthesis also includes a compressible body disposed in the closed chamber and located between the plates. The compressible body has a first surface in contact with a face of one of the plates, whereby an area of contact between the first surface of the compressible body and the face of the one of the plates increases when compressive forces are exerted upon the compressible body.

38 Claims, 3 Drawing Sheets

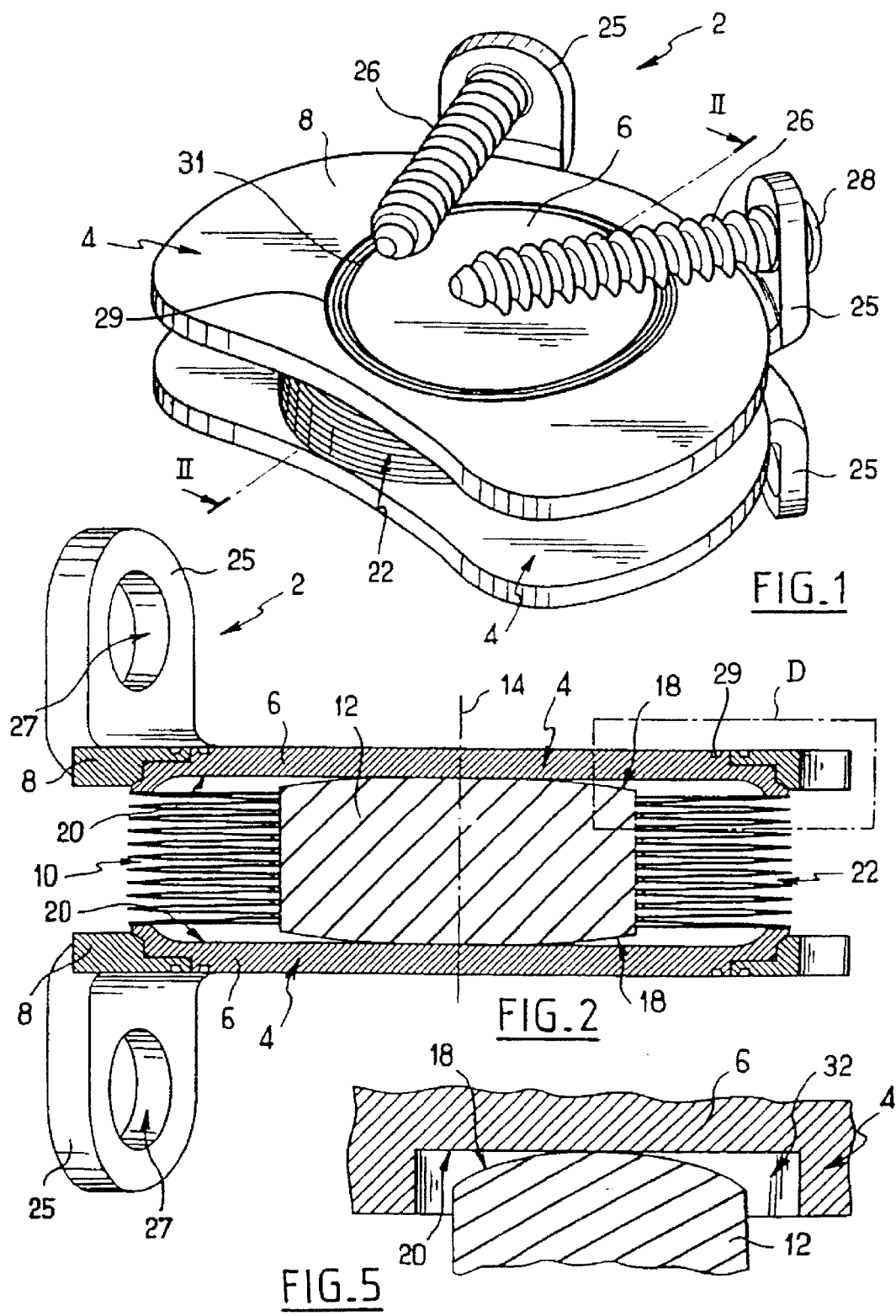

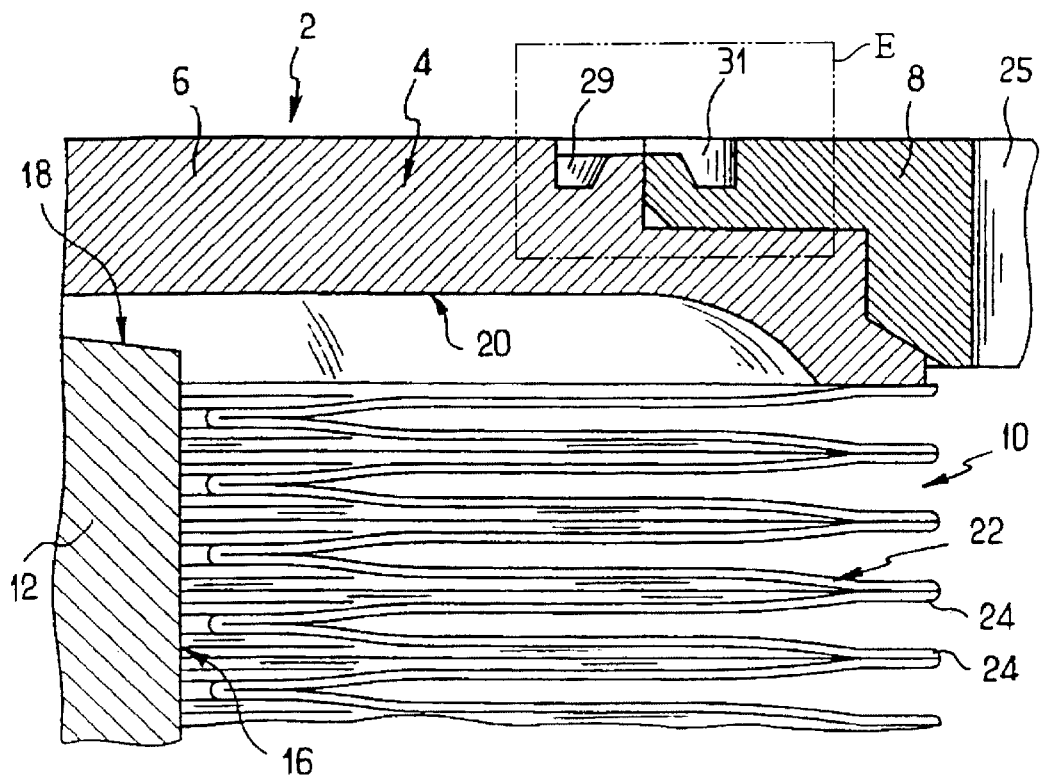
FIG_3
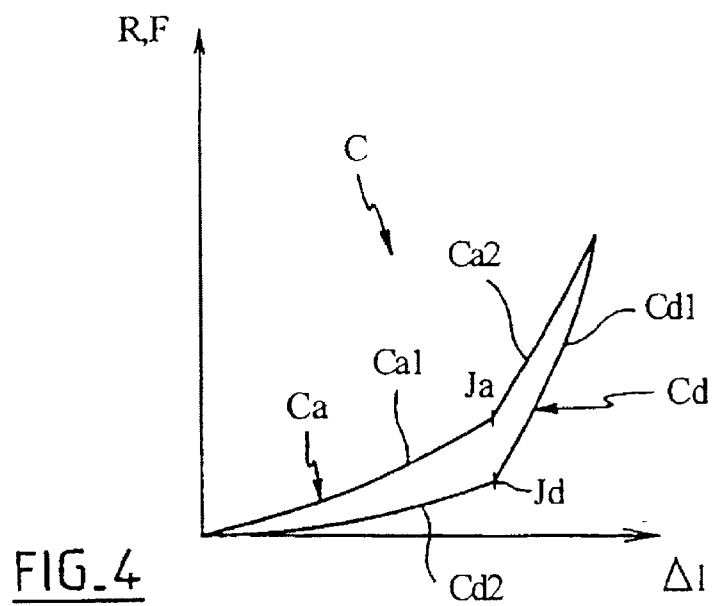
FIG_4

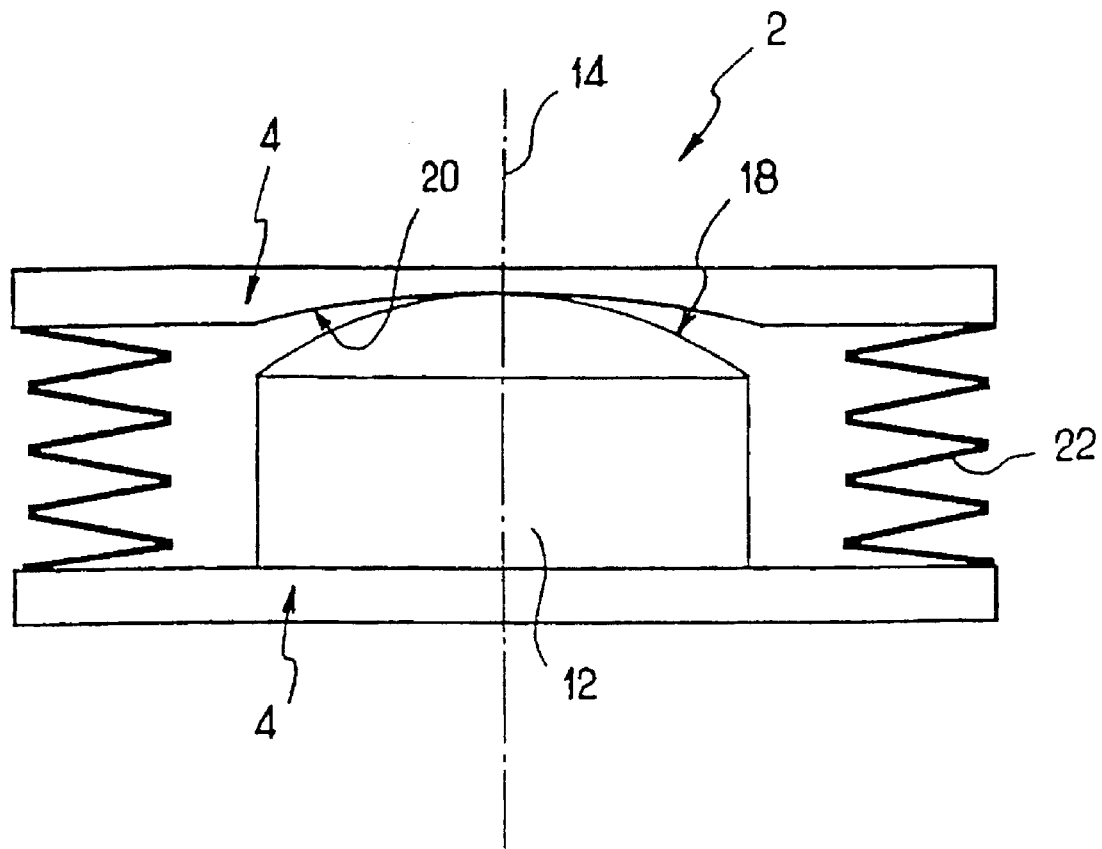
FIG_6
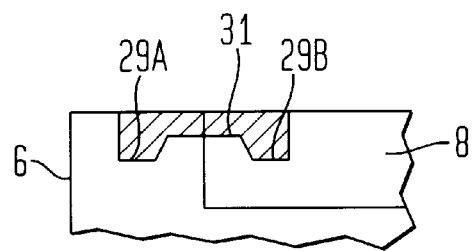
FIG_7

US 6,582,468 B1

INTERVERTEBRAL DISC PROSTHESIS WITH COMPRESSIBLE BODY

BACKGROUND OF THE INVENTION

The invention relates to intervertebral disc prostheses. The document EP-0 356 112 discloses an intervertebral disc prosthesis comprising two generally flat plates and an elastomeric body interposed between the plates and fixed to them by its flat end faces. The mechanical behavior of this prosthesis is quite similar to that of a natural healthy intervertebral disc, especially when the body is compressed between the two plates.

SUMMARY OF THE INVENTION

One object of the invention is to provide a disc prosthesis of a different type that more closely approximates to the mechanical properties of a natural healthy intervertebral disc.

To achieve this object, the invention provides an intervertebral disc prosthesis comprising two plates and a compressible body interposed between the plates, at least one end of which has an area of contact with one of the plates, in which prosthesis the body and the plate are such that the area of contact increases when a stress on the plate in the direction of the body is increased.

Thus, when the compressive stress on the body increases from a moderate value or zero, the height of the body, measured from one plate to the other, reduces relatively quickly. Subsequently, as the contact area increases, the reaction of the body becomes greater and a comparatively greater stress has to be applied to reduce the height by an equivalent amount. In other words, for the lowest compression values the mechanical reaction of the body during the compression varies very little as a function of the change of height. Consequently, the curve representing the applied stress as a function of the variation of height is inclined only a small amount from the horizontal for low compression values. At the beginning of the stroke, therefore, the load supplied is small. This property is also that of a natural healthy disc. The behavior of the body can therefore be adapted not only by the choice of material but also by the shape of the end face or faces with a contact area which varies so as to approximate as closely as possible to the mechanical properties of a natural healthy intervertebral disc.

Advantageously, the area of contact is defined by a face of the plate and a face of the end of the body, one of the faces of the plate or of the body, notably the face of the body, being curved and convex, and the other face being flat.

Advantageously, the area of contact is defined by a face of the plate and a face of the end of the body, both faces being curved in at least one common direction, and one being concave and the other convex, the concave face having at least one radius of curvature greater than a corresponding radius of curvature of the convex face.

This configuration therefore enables the variations of mechanical reaction to be introduced as indicated above. Furthermore, when the body is free to move sideways with respect to the plate, as will be seen later, this configuration ensures the relative centering of the two faces. For example, after the two faces have been displaced relative to each other, these curvatures enable them to recenter themselves automatically.

Advantageously, the body has at least one end in contact with one of the plates and free to move with respect to the plate in a direction parallel to the plate.

This arrangement therefore reduces the risk of excessive stress developing between the two vertebrae in a direction perpendicular to the longitudinal direction of the spine, that is to say in shear.

Advantageously, the body has an end housed in a depression in one of the plates that forms a lateral stop for this end.

Lateral displacements of the body relative to the plate can therefore be limited or even prevented.

Advantageously, the body comprises a viscoelastic material, notably silicone.

With such a material it is possible to give a hysteresis form to the curve representing the stress on the compressed body relative to its changing height. Since this curve is also that of a natural healthy disc, its mechanical properties are approximated to even more closely.

The prosthesis advantageously comprises a fluid interposed between the plates.

The addition of a fluid therefore increases the hysteresis form, especially when the fluid is compressible such as a gas or a mixture of a liquid and a gas which is partially soluble in the liquid.

Advantageously, the fluid is in contact with the plates.

Advantageously, the fluid is around the periphery of the body.

Advantageously, the prosthesis comprises an enclosure containing the fluid and constructed in such a way that it has a cross-sectional area parallel to the plates that is effectively invariable when a stress pushing the plates toward each other varies.

Advantageously, the prosthesis is intended for the lumbar region of the spine.

Other features and advantages of the invention will also appear in the following description of a preferred embodiment and two variants given by way of non-limiting examples.

BRIEF DESCRIPTION OF THE DRAWINGS

FIG. 1 is a perspective view of a prosthesis according to the invention;

FIG. 2 is a view in axial section on plane II—II of the prosthesis shown in FIG. 1;

FIG. 3 is a view on a larger scale of a detail D indicated in FIG. 2;

FIG. 4 is a curve indicating the compressive force F exerted by the two plates on the cushion as a function of the variation of the distance between them;

FIG. 5 is a sectional view of a detail of a variant of the prosthesis; and

FIG. 6 is a simplified view similar to FIG. 2 showing a second variant.

FIG. 7 is a view on a larger scale of a detailed E indicated in FIG. 3.

DETAILED DESCRIPTION

The intervertebral disc prosthesis 2 according to the invention is particularly intended in this case for the lumbar region of the vertebral column of the human body. It comprises two plates 4 in the general shape of a bean with the hilum on the posterior sides seen in plan view. Each plate 4 comprises a central circular dish 6 and a ring 8 extending around the periphery of the circular dish, in the plane of the circular dish. At rest, the two plates 4 lie parallel to each other at a distance facing each other so that their outlines coincide. On each plate 4, the ring 8 and the circular dish 6 each have a groove 29 to house a seal 31.

The disc prosthesis 2 comprises a cushion or intermediate part 10 interposed between the two plates 4. The cushion comprises a compressible solid body 12, in this case made of viscoelastic material, for example silicone. This body has a Shore A hardness of advantageously between 60 and 100, in this case approximately 80. The body 12 is a body of revolution about its minor axis 14. It has a cylindrical lateral face 16 and two faces at the axial ends 18 which are generally perpendicular to the axis 14 and of slightly spherical convex shape. Each face 18 therefore has two identical curvatures in planes perpendicular to each other. The body 12 is arranged coaxially with the circular dishs 6. Each circular dish 6 has a plane internal central face 20 perpendicular to the axis 14 and in contact with a respective axial end 18 of the body 12. The convex spherical face 18 of the body therefore rests against the plane face 20 of the plate. The body 12 rests without mechanical connection against each of the plates 4 in such a way that it is able to move with respect to each of these plates in a direction parallel to the circular dishs, that is to say perpendicular to the minor axis 14. In this way, lateral stresses are not transmitted from vertebra to vertebra.

The cushion 10 also includes a bellows 22. The bellows surrounds the body 12 coaxially with it and at a distance from it. It is a symmetrical body of revolution about the axis 14. Its wall in profile has corrugations 24 that enable the length of the bellows 22 to be varied along the axial direction 14, without significantly varying the surface area of its cross section at right angles to the axis 14. In the present case, the bellows, like the plates 4, is made of titanium or titanium alloy, so that it has a certain axial rigidity and forms a compression spring. It can also be deformed in a direction perpendicular to the axis 14 or undergo torsion about the axis 14 or about any axis perpendicular thereto.

At both its axial ends, the bellows 22 has edges bonded to respective edges of the circular dishs 6 which project from the inside face 20. The bond is made leaktight so that the bellows 22 defines with the two circular dishs 6 a sealed variable-volume enclosure extending around the body 12. This enclosure contains a fluid, in this case a gas which in this case is air. The corrugations 24 closest to the body 12 are at a distance from it to allow free movement of gas from one to the other of the circular dishs 6.

The bellows 22 in the present case has ten convolutions, i.e. eight external crests in addition to the two crests attached to the plates. It has here an outside diameter of about 30 mm and an inside diameter of about 17 mm. Its height, when the prosthesis is not under load, is 10 mm. The wall of the bellows can be made from one, two, or three sheets each 0.1 mm thick, the sum of the thicknesses forming the thickness of the wall. The stiffness of the bellows on its own here is approximately 1.6 N/mm.

Each annulus 8 comprises two lugs 25 projecting from an outside face of the plate 4 at right angles to the plane of the plate. Each lug 25 contains an orifice 27 passing all the way through it and directed toward the center of the circular dish and, on a face of the lug 25 turned away from the plate 4, a spherical impression. The orifices 27 are to accommodate a bone screw 26 with a head 28 whose underside has a male spherical shape engaging with the female impression of the lug 25 so as to allow free orientation of the screw 26 with respect to the associated lug.

For short-term anchoring of the disc prosthesis 2 in the column, the screws 26 can be anchored in the spondyl of the vertebrae adjacent to the disc to be replaced.

However, a so-called long-term anchoring can be provided in which, in addition, the surfaces of the plates 4 in contact with the adjacent vertebrae are covered with hydroxyapatite, or any other substance known per se capable of stimulating bone growth. Before covering them, the said surfaces can be treated to obtain a more or less porous surface condition with anchor points for the bone tissue, in order to create a better interface with said bone tissue.

Shown in FIG. 4 is the curve C indicating the intensity of a compressive load F applied to the cushion 10 (that is to both plates 4), taking no account of their deformability (which is practically zero), in the axial direction 14, as a function of the variation of the length 1 of the cushion in the axial direction 14 (or of the distance between the two plates). This curve also represents the mechanical reaction R of the cushion 10 under the same conditions.

This curve C is not linear. Furthermore, it exhibits hysteresis: the curve Ca indicating the increase in the compression F from the origin zero is separate from the curve Cd indicating the decrease in the compression F down to the origin, and is at all points above it. This pronounced hysteresis form is due principally to the viscoelastic material of the body and to a lesser extent to the combination in the cushion 10 of the body 12 and of the fluid.

Moreover, the curve Ca, relating to the increase in the compressive force F, exhibits beginning at the origin O a portion Ca1 of shallow gradient followed by a portion Ca2 of steeper gradient. The curve Cd illustrating the decrease in the compression F exhibits for the highest values of the force F a portion Cd1 of steep gradient, followed by a portion Cd2 of shallower gradient for the lowest values of the force F. The presence of a portion of shallow gradient in the vicinity of the origin in the case of the curves Ca and Cd is due principally to the conforming of the contacting faces 18, 20 of the body 12 and of the plates 4, which has the effect that the area of mutual contact between each plate and the body, which is generally in the form of a disc, increases with the force F. This increase continues until the maximum surface of the contact area is reached, when the whole of the face 18 is touching the plate 4.

The junction points Ja and Jd form the junctions between the curves Ca1 and Ca2, and Cd1 and Cd2, respectively. In the curve Ca, the point Ja corresponds to the load F at which the maximum contact areas have been reached between the plates and the body. Likewise in the curve Cd, the point Jd corresponds to the load at which these areas cease to be maximum.

The prosthesis can be configured in such a way that the point Ja corresponds to a value $\Delta 1$ situated between 25% and 75% of the maximum variation of length envisioned for the prosthesis in use.

Referring to FIG. 5, it is possible in a variant (which in other respects has the other characteristics of the prosthesis shown in FIG. 1), for the face 20 of each plate 4 facing the body 12 to have a depression 32, U-shaped in this case, forming a lateral stop, in which the corresponding axial end 18 of the body sits. Any sideways relative displacements of the body 12 with respect to each plate 4 are thus kept within a certain range, or even prevented altogether.

In the variant shown in FIG. 6, the face 20 of the plate may be curved and concave in one or two directions, as is the case here, and the face 18 can be curved and convex in the corresponding direction or directions, the radius of curvature of the face 20 being, for each direction, greater than that of the face 18 in the corresponding direction. Both faces 18, 20 here are spherical. The radii of curvature of the surfaces 18 and 20 will be for example between 70 and 80 mm, and 140 and 200 mm, respectively. Such an arrangement offers selfcentering of the two faces while permitting sideways relative displacement of the body 12 with respect to the plate in any direction perpendicular to a longitudinal direction of the spine.

In the embodiment shown in FIG. 2, both ends of the body 12 have a surface 18 in contact with the associated plate, the area of which is variable and which makes it able to move sideways with respect to the body.

By contrast, in the variant shown in FIG. 6, only one of the ends 18 of the body 12 has this property. The other end, which is the lower end in FIG. 6, has a plane circular shape whose area of contact with the associated plate is invariable and fixed with respect thereto.

FIG. 7 shows circular dish 6 having a first groove 29A and ring 8 having a second groove 29B. A seal 31 is disposed in the grooves 29A, 29B for providing a seal between the opposing edges of circular dish 6 and ring 8.

It is of course possible to make numerous modifications to the invention without departing from its scope.

The fluid may be a liquid, or even a mixture of a liquid and a gas, the latter being for example slightly soluble in the liquid.

The body may be elliptical in cross section through the axis 14.

The inside faces 20 of the plates 4 may be convex, the axial end face 18 of the body 12 being flat, or concave with a greater radius of curvature than the radius of the face 20 of the plate. The two contacting faces of the plate and of the body may be convex.

The curvature of the faces may be limited to a single plane.

The characteristics relating to the envelope 22 (spring, distance from the body 12) may be used independently of the other characteristics.

What is claimed is:

1. An intervertebral disc prosthesis comprising:
   two opposing plates;
   a flexible seal extending between said two opposing plates for forming a closed chamber between said two plates, wherein said flexible seal is adapted for enabling said plates to move relative to one another; and
   a compressible body disposed in said closed chamber and between said plates, said compressible body having a first surface in contact with a face of one of said plates, wherein an area of contact between the first surface of said compressible body and the face of said plate increases when compressive forces are exerted upon said compressible body; and
   a fluid provided in said closed chamber between said two opposing plates, wherein said fluid is in contact with said plates and surrounds said compressible body.

2. The disc prosthesis as claimed in claim 1, wherein said compressible body has a second face opposite the first face, wherein the first face is in contact with a first one of the two plates and the second face is in contact with a second one of the two plates.

3. The disc prosthesis as claimed in claim 2, wherein said compressible body has a normal height measured from the first plate to the second plate, and wherein the height of said body reduces when compression forces are exerted upon one of more of said plates.

4. The disc prosthesis as claimed in claim 1, wherein the first face of said body defines a convex, curved surface having an apex in contact with the one of said plates, and a face of the one of said plates in contact with the first face of said compressible body is substantially flat.

5. The disc prosthesis as claimed in claim 1, wherein the first face of said body is convex, and a face of the one of said plates in contact with the first face is concave, and wherein the concave face of the plate has a radius of curvature that is greater than a radius of curvature of the convex first face of said compressible body.

6. The disc prosthesis as claimed in claim 1, wherein the face of said plate in contact with said compressible body has a depression, and wherein the first surface of said compressible body is at least partially disposed in the depression.

7. The disc prosthesis as claimed in claim 6, wherein said depression is adapted to limit lateral displacement of said compressible body relative to said plate.

8. The disc prosthesis as claimed in claim 1, wherein said compressible body comprises a viscoelastic material.

9. The disc prosthesis as claimed in claim 8, wherein said compressible body comprises silicone.

10. The disc prosthesis as claimed in claim 1, wherein said fluid is compressible.

11. The disc prosthesis as claimed in claim 10, wherein said fluid is selected from the group consisting of liquids, gases and mixtures of liquids and gases.

12. The disc prosthesis as claimed in claim 1, wherein said plates are sized and shaped for the lumbar region of a vertebral column.

13. The disc prosthesis as claimed in claim 1, wherein at least one of said plates includes a central circular dish, a ring extending around an outer periphery of the central circular dish, at least one groove extending between said circular dish and said ring, and a seal housed in said at least one groove.

14. The disc prosthesis as claimed in claim 1, wherein said compressible body has a Shore A hardness rating of approximately 60–100.

15. The disc prosthesis as claimed in claim 14, wherein said compressible body has a Shore A hardness rating of approximately 80.

16. The disc prosthesis as claimed in claim 1, wherein said compressible body has the first surface thereof in contact with a first one of said plates, a second surface thereof in contact with a second one of said compressible plates, and a substantially cylindrical sidewall extending between the first and second surfaces of said compressible body.

17. The disc prosthesis as claimed in claim 16, wherein the first and second surfaces of said compressible body have a spherical convex shape.

18. The disc prosthesis as claimed in claim 17, wherein the spherical convex surfaces of said first and second surfaces have radii of curvature that are substantially similar to one another.

19. The disc prosthesis as claimed in claim 13, wherein said compressible body is in contact with the central circular dish.

20. The disc prosthesis as claimed in claim 13, wherein said compressible body has a major axis that is in substantial alignment with a center point of said central circular dish.

21. The disc prosthesis as claimed in claim 1, wherein said two opposing plates normally lie in planes that are substantially parallel to one another, and wherein said compressible body is movable in directions parallel to the normally parallel planes of said plates.

22. The prosthesis as claimed in claim 1, wherein at least one of said plates is securable to bone.

23. The prosthesis as claimed in claim 22, wherein the at least one of said plates securable to bone has at least one lug projecting therefrom, said lug having an orifice adapted to receive a screw insertible into the bone.

24. The prosthesis as claimed in claim 1, wherein said flexible seal includes a bellows having an upper edge secured to one of said plates and a lower edge secured to the other of said plates.

25. The prosthesis as claimed in claim 13, wherein said flexible seal includes a bellows having an upper edge secured the central circular dish of a first one of the plates and a lower edge secured to the central circular dish of a second one of the plates.

26. The prosthesis as claimed in claim 25, wherein the upper and lower edges of said bellows are bonded to outer edges of said respective circular dishes.

27. The prosthesis as claimed in claim 25, wherein said bellow has a stiffness of approximately 1.6 N/mm.

28. The prosthesis as claimed in claim 1, wherein said plates have outer surfaces covered with a bone-growth stimulating material.

29. The prosthesis as claimed in claim 28, wherein said bone-growth stimulating material comprises hydroxyapatite.

30. The prosthesis as claimed in claim 1, wherein said plates have a porous outer surface covered with a bone growth stimulating material.

31. The prosthesis as claimed in claim 1, wherein a second surface of said compressible body remote from the first surface thereof is substantially flat and in contact with a flat face of a second one of the two opposing plates.

32. The prosthesis as claimed in claim 1, wherein said compressible body is elliptical in cross section.

33. The prosthesis as claimed in claim 1, wherein said opposing plates are compressible toward one another along a main axis of compression.

34. The prosthesis as claimed in claim 1, wherein said flexible seal normally maintains said opposing plates at a first spaced distance relative to one another when no compression forces are applied to said plates.

35. The prosthesis as claimed in claim 34, wherein said opposing plates are compressible to a second spaced distance that is less than said first spaced distance when compression forces are applied to said opposing plates.

36. The prosthesis as claimed in claim 35, wherein the spaced distance of said plates relative to one another as a function of the compression forces applied to said plates follows a graph curve having a hysteresis form.

37. An intervertebral disc prosthesis comprising:
    two opposing plates movable relative to one another;
    a flexible seal extending between said two opposing plates for forming a closed chamber therebetween;
    a compressible body disposed in said closed chamber and between said opposing plates, said compressible body having a first surface in contact with a face of one of said plates; and
    a fluid provided in said closed chamber in contact with said opposing plates and surrounding said compressible body, wherein an area of contact between the first surface of said compressible body and the face of one of said plates increases when compressive forces are exerted upon said compressible body.

38. The disc prosthesis as claimed in claim 37, wherein the first surface of said compressible body is curved, convex in shape, wherein an apex of said curved, convex surface engages a substantially flat face of the one of said plates.

* * * * *

UNITED STATES PATENT AND TRADEMARK OFFICE
CERTIFICATE OF CORRECTION

PATENT NO. : 6,582,468 B1 Page 1 of 1
DATED : June 24, 2003
INVENTOR(S) : Fabien Gauchet It is certified that error appears in the above-identified patent and that said Letters Patent is hereby corrected as shown below:

Title page,
Item [73], "Spryker" should read -- Stryker --.

Column 2,
Line 54, "detailed" should read -- detail --.

Column 3,
Lines, 13, 38 and 40, "dishs" should read -- dishes --.
Line 21, "minor" should read -- main --.

Column 5,
Line 3, "selfcentering" should read -- self-centering --.
Line 65, "of" should read -- or --.

Column 7,
Line 9, after "secured" insert -- to --.
Line 16, "bellow" should read -- bellows --.

Signed and Sealed this

Seventh Day of October, 2003

JAMES E. ROGAN
*Director of the United States Patent and Trademark Office*